United States Patent [19]
Adrian

[11] Patent Number: 5,810,860
[45] Date of Patent: Sep. 22, 1998

[54] EASILY FABRICATED ROTARY-DRIVE ACOUSTIC ABLATION CATHETER

[75] Inventor: Sorin Adrian, Penn Valley, Pa.

[73] Assignee: Medelex, Inc., Penn Valley, Pa.

[21] Appl. No.: 829,052

[22] Filed: Mar. 31, 1997

[51] Int. Cl.⁶ .................................................. A61B 17/00
[52] U.S. Cl. .......................................... 606/169; 606/171
[58] Field of Search ................... 604/22; 606/1, 606/167, 169, 171, 177

[56] References Cited

U.S. PATENT DOCUMENTS

5,423,797  6/1995  Adrian et al. ............................ 606/1
5,593,415  1/1997  Adrian .................................... 606/169

*Primary Examiner*—Michael Powell Buiz
*Assistant Examiner*—David O. Reip
*Attorney, Agent, or Firm*—William H. Meise

[57] ABSTRACT

An acoustic ablation catheter driven by a rotating shaft (18) includes a rotary-to-axial-motion converter (210), which includes a rotary driver (220, 420) in the form of a shell (222, 422) defining an inner surface (228, 428) which features a depressed groove (230, 330, 430). A follower (250, 490, 724) includes protuberance(s) (254, 494) which extend radially outward to engage the groove. This arrangement provides higher frequency response than some prior-art arrangements, and has the advantage of lesser diameter. In a particular embodiment, the shell (422) is made up of a cylinder (422) with a smooth interior, together with two end pieces (470, 480) which have axially-directed bumps or teeth (472, 482) which together define the guide path (330, 430). In a particular embodiment of the invention, the body (12) of the catheter (10) is made from a braided tube impregnated with a cured liquid, such as polymer. The body of the catheter is made by braiding threads to form a tube, expanding the tube to fit over a mandrel having the shape of the body of the catheter, impregnating the braided tube with uncured liquid polymer, vacuum bagging the impregnated tube and the mandrel, and curing the impregnant.

8 Claims, 5 Drawing Sheets

EASILY FABRICATED ROTARY-DRIVE ACOUSTIC ABLATION CATHETER

FIELD OF THE INVENTION

This invention relates to catheters for medical uses, and more particularly to acoustic ablation catheters using rotary-to-axial motion converters.

BACKGROUND OF THE INVENTION

U.S. Pat. No. 5,423,797, issued Jun. 13, 1995 in the name of Adrian et al. describes an ablation catheter which includes a rotary-to-axial motion converter at its distal end, driven by a rotating shaft. The motion converter converts the rotary motion of the shaft into axially-directed pulsations, which are coupled to the surrounding fluid to thereby generate the acoustic energy by which ablation is accomplished. In one embodiment described therein, the motion converter includes an uneven or wavy surface or swash plate which is rotated by the shaft, and a follower which is free for axial motion, which bears against the wavy surface, and is pushed distally by the protruding portions of the surface. In one embodiment of the catheter, the follower is returned to its proximal position by a spring arrangement. It has been found that, for some frequencies, the restoring force available from a spring arrangement may not be sufficiently great to provide the acceleration of the follower which is required to return the follower to its proximal position before the next distally-projecting portion of the wavy surface is in place. This, in turn, tends to impose an upper limit on the useful frequency of the rotary-to-axial motion converter.

Figure 1A:
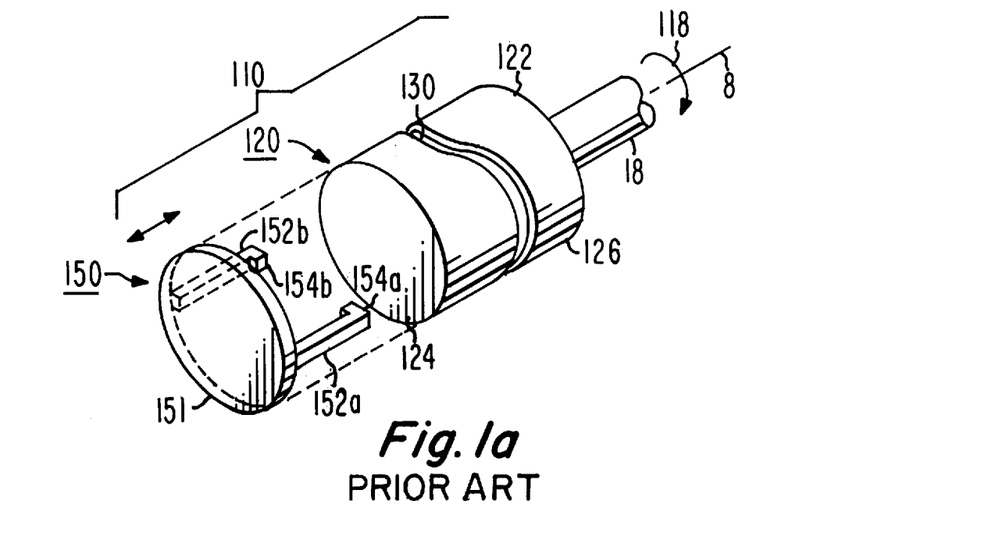
FIG. 1a is a simplified perspective or isometric view, exploded to illustrate separate parts, of a prior-art rotary-to-axial motion converter which can be used in an ablation catheter.
Figure 1B:
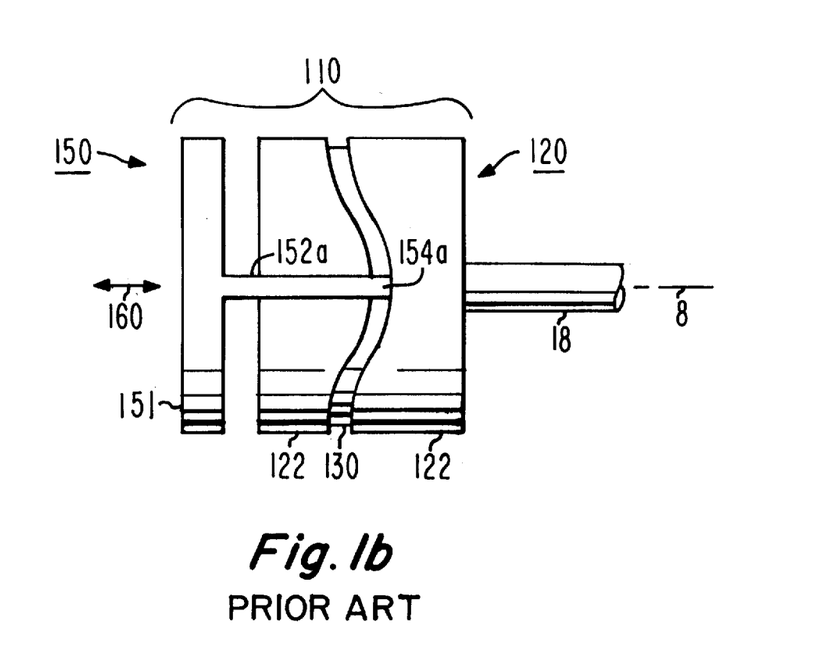
FIG. 1b is a side view thereof in its assembled form.

In another embodiment of the invention of the abovementioned Adrian et al. patent, illustrated in FIGS. 1a and 1b, the rotary-to-axial motion converter 110 includes a follower 150 with a body 151, and with arms 152a, 15b, which have tabs or protrusions 154a, 154b at their proximal ends. The arms 152a, 152b extend over the body 124 of the rotary driver 120 to engage a depressed groove 130 which imparts the back-and-forth axial motion when the rotary driver 120 is driven by the shaft 18. This arrangement returns the follower 150 to its proximal position by the force of the rotary driver, avoiding the limitations of the return spring.

Improved acoustic catheters are desired.

SUMMARY OF THE INVENTION

An acoustic ablation catheter according to the invention comprises an elongated catheter body defining distal and proximal ends. An elongated drive shaft extends from near the proximal end to near the distal end of the catheter body. A coupling arrangement is coupled to the shaft at a location near the proximal end of the body, adapted for coupling the shaft to a rotary driver, such as an electric motor, whereby, when so coupled, the shaft is driven in a rotary manner. A rotary-to-axial motion converter is coupled to the shaft near the distal end of the catheter body, for, when driven in a rotary manner by the shaft, converting the rotary motion into axial motion.

The rotary-to-axial motion converter of the catheter further comprises a rotary driver coupled to the shaft, for being driven in a rotary manner thereby in response to rotation of the shaft. The rotary driver includes a cylindrical shell with an outer surface having the general outer shape of a right circular cylinder. defining distal and proximal ends. The cylindrical shell also defines an inner surface with a guide path which is circumferentially continuous about the circumference of the inner surface of the shell. The guide path has portions which lie closer to the distal end of the cylindrical shell and other portions which lie closer to the proximal end of the shell.

The rotary-to-axial motion converter of the catheter also comprises a follower coupled to the guide path. The follower is fixed against rotation, so it cannot rotate with the rotary driver. The follower is mechanically coupled to the guide path, for being reciprocally driven in an axial manner in response to rotation of the shaft, shell, and guide path. This arrangement has the advantage of minimizing the diameter of the rotary-to-axial-motion converter relative to that of FIGS. 1a and 1b.

In a particular embodiment of the invention, the catheter body is flexible, so that its shaft defines a local axis at various locations along the catheter. The cylindrical shell is centered about at least an extension of the local axis. The guide path is in formed by, or includes or comprises, a depressed groove formed in the inner surface of the cylindrical shell; this depressed groove is depressed relative to the cylinder inner surface "land" area. The follower includes at least one tab or projection extending radially away from the local axis for being mechanically coupled to the depressed groove of the cylindrical shell. When the shaft rotates, the cylindrical shell rotates, carrying the depressed-groove guide path with it. The follower projection rides in the groove, and is therefore translated axially with a continuous reciprocal motion.

In a particularly advantageous embodiment of the invention which is relatively easy to fabricate, the. cylindrical shell and the depressed-groove guide path is made up of at least a cylindrical shell having a smooth inner surface, together with one or more end pieces or inserts, which may be annular or solid. The end pieces are dimensioned to fit at the end of the cylinder or within the cylinder, and have axial projections which define portions of the depressed groove guide path. The follower includes at least one tab or radial projection which fits into the guide path. When the shaft rotates, the cylinder and its inner groove rotates, and at a fixed point around the periphery of the groove, the groove effectively moves in with a reciprocal axial motion. The tab or projection of the follower is mechanically coupled to the groove, and the follower itself is prevented from rotating, and as a consequence the tab or projection, and the follower itself, moves axially with a reciprocal motion.

BRIEF DESCRIPTION OF THE DRAWING

FIG. 2c is a developed view of the groove in the inner surface of the shell of FIG. 1a;

DESCRIPTION OF THE INVENTION

The arrangement according to the invention avoids having the shaft drive not only the mass of the biological fluid during the compression stroke of the follower, but also the return spring of the prior-art catheter, and of having no load on the shaft during the return stroke. During the forward movement of the follower of the prior-art arrangements, the swash plate, and implicitly the motor, must develop enough energy to move the follower forward or distally, to displace the biological material in front of the follower, and to compress the return spring. Better performance is achieved by operating at resonance, at which transfer of energy between the rotational and longitudinal motions is optimized. Springs with high stiffness constant are desired in order to achieve resonance in the ultrasonic range. The use of stiff springs, however, requires that the driver have high starting and running torque in order to achieve resonance. When operating at resonance, the swash plate supplies just enough energy to the follower to compensate for energy lost to generation of the desired vibration and heat. This arrangement, however, requires, in addition to a higher-torque motor, and a thicker shaft to carry the higher torque. The spring also undesirably tends to increase the size of the motion converter head.

FIGS. 1a and 1b illustrate the substantive portion of a rotary-to-axial-motion converter 110 of a catheter described in U.S. Pat. No. 5,423,797, issued Jun. 13, 1995 in the name of Adrian et al. In FIGS. 1a and 1b, a prior-art catheter includes a rotary driver 120 and a follower 150. Rotary driver 120 is in the form of a right circular cylindrical surface 122 defining a distal end 124 and a proximal end 126. As illustrated in FIGS. 1a and 1b, rotary driver 120 is connected at its proximal end 126 to a flexible shaft 18, which, in use, drives the rotary driver in the direction illustrated by arrow 118. The cylindrical surface 122 of rotary driver 120 defines a depressed groove 130, which extends completely about the circumference of surface 122 of rotary driver 120, to form a continuous path. Groove 130 defines a sinusoidal path. Follower 150 includes a body 151 and a pair of proximally-extending legs 152a and 152b. Each leg terminates in an inwardly-projecting tab or projection 154a, 154b, which is dimensioned to be accommodated within the groove 130. As described in the Adrian et al. patent, rotation of the rotary driver by the shaft 18 causes the rotary drive cylinder 120 with its groove 130 to rotate about the local axis, which is the axis of the catheter in the region being considered. When the rotary drive cylinder rotates with its groove, the projections 154a and 154b are reciprocally moved axially in the direction of arrow 160 of FIG. 1b.

Figure 2A:
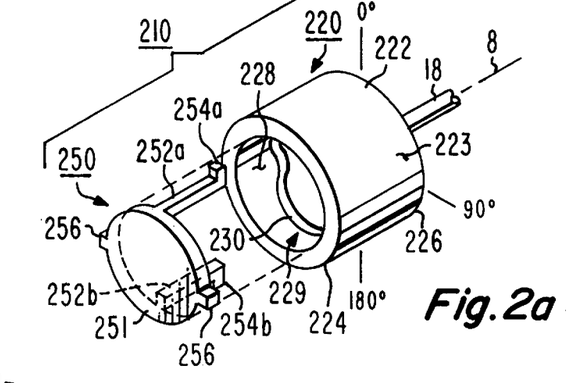
FIG. 2a is a simplified perspective or isometric view, exploded to reveal separate parts, of a rotary-to-axial motion converter according to an aspect of the invention, which includes a shell with a guide path in the form of an internal groove.
Figure 2B:
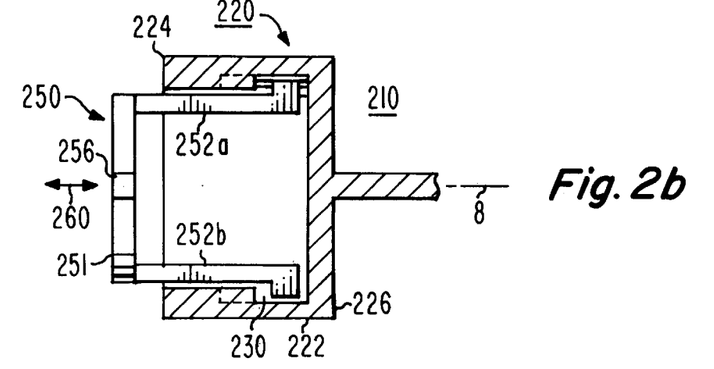
FIG. 2b is a cross-sectional side view thereof in its assembled form.

FIGS. 2a and 2b illustrate a rotary-to-axial-motion converter 210 in accordance with an aspect of the invention. As illustrated in FIGS. 2a and 2b, converter 210 includes a rotary driver 220 and a follower 250. Rotary driver 220 is in the form of a right circular cylindrical shell 222 defining an outer surface 223, a distal end 224, and a proximal end 226. As illustrated in FIGS. 2a and 2b, rotary driver 220 is connected at its proximal end 226 to a flexible shaft 18, which, in use, rotationally drives the rotary driver 220. The outer cylindrical surface 223 of shell 222 of rotary driver 220 is plain. The shell 222 defines an inner surface 228, which defines a depressed groove 230, which extends completely about the circumference of inner surface 228 of shell 222 of rotary driver 220, to form a continuous path. Groove 230 defines a sinusoidal path. Follower 250 includes a body 251 and a pair of proximally-extending legs 252a and 252b. Each leg terminates in an inwardly-projecting tab or projection 254a, 254b, which is dimensioned to be accommodated within the groove 230. Rotation of the rotary driver cylinder 220 by the shaft 18 causes the rotary drive cylinder 220 with its internal groove 230 to rotate about the local axis 8. When the rotary drive shell 222 rotates with its groove 230, the projections 254a and 254b are reciprocally moved axially in the direction of arrow 260 of FIG. 2b.

Figure 2C:
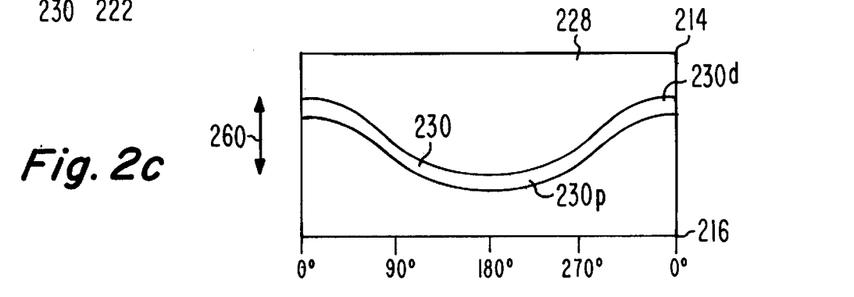

FIG. 2c is a developed view of the internal surface 228 of the shell 222 of FIGS. 2a and 2b, with the angles plotted along the abscissa corresponding to the angles illustrated in FIG. 2a. In FIG. 2c, the sinusoidal nature of the groove 230 in the inside "land" surface 228 of the shell is apparent, with a distal portion 230d of the groove 230 being closest to distal end 214 of the shell, and with a proximal portion 230p nearest the proximal end 216 of the shell. Those skilled in the art realize that the 0° markings at the right and left sides of the developed view means that the right and left sides of the groove are at the corresponding location, so that the groove 230 is circumferentially continuous, without breaks.

Figure 3:
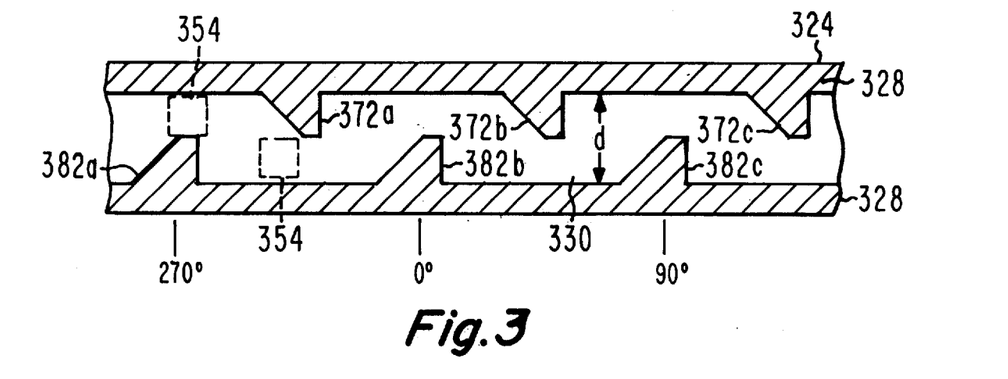
FIG. 3 is a developed view of a guide path in the form of a groove in the inner surface of a shell in accordance with another aspect of the invention.

FIG. 3 is a developed view of a depressed groove in the interior surface of a shell, in accordance with another aspect of the invention. In FIG. 3, the land areas 328 are hatched for clarity, but the hatching has no significance except to make the non-hatched groove 330 stand out. As illustrated in FIG. 3, the groove 330 is formed by axial ramp-like extensions of the land areas 328 projecting into a "smooth" groove. Thus, groove 330 may be thought of as starting as a smooth groove having a width illustrated as "d" without axial excursions, but wider than necessary to accommodate the pins or tabs of a follower, which are illustrated in phantom, at different positions along the groove, as squares 354. The axial projections then impart a "waviness" to the smooth groove, to make groove 330. The projections or ramps which are proximally-directed are designated as 372a, 372b, 372c, . . . , and the distally-projecting ramps are designated 382a, 382b, 382c, . . . . In a way, the guide path 330, when developed about an axis of the catheter as illustrated in FIG. 3, traces a path including ramp-like projections 372, 382, which alternate between distally-directed ramps 372 and proximally-directed ramps 382. This arrangement has the advantage of being easier to fabricate with simple tools than a smooth, sinusoidal groove such as that illustrated in conjunction with FIG. 2c. Further, it would be very difficult to cut a groove such as that of FIG. 2c where the groove includes discontinuities such as abrupt changes of direction.

Figure 4A:
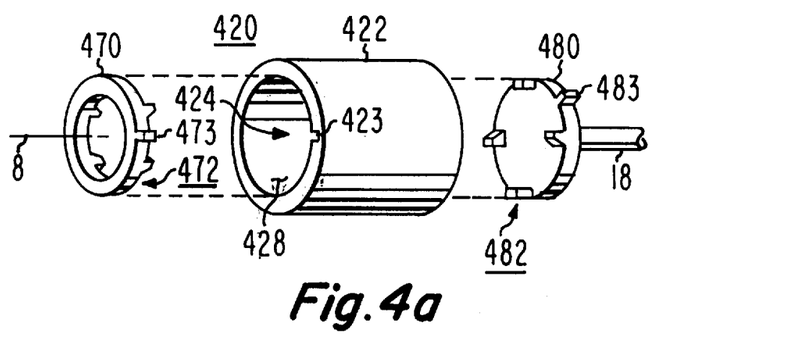
FIG. 4a is an exploded perspective or isometric view of two end pieces which together define the bearing portions of a guide path in accordance with an aspect of the invention, together with a shell with which they may be associated to form a rotary driver.
Figure 4B:
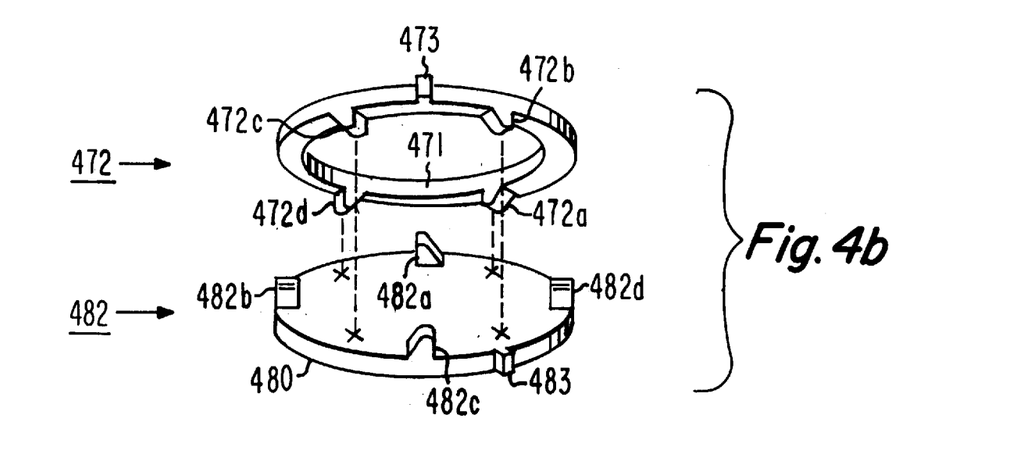
FIG. 4b is an exploded view of the two end pieces of FIG. 4a, and FIG. 4c is a simplified perspective or isometric view, exploded, of the rotary driver of FIG. 4b, in conjunction with a follower.

FIG. 4a illustrates a rotary driver 420 which includes a cylindrical shell 422 with two end pieces 470 and 480, and FIG. 4b illustrates the end pieces in more detail. As illustrated in FIGS. 4a and 4b, the end pieces are in the general shape of circular plates 470 and 480, which are dimensioned to fit within a cavity or open space 428 of shell 422. In FIG. 4b, distal end plate 470 has a central aperture 471, and a plurality of teeth or proximally-projecting bumps of a set 472, individually designated 472a, 472b, 472c, and 472d. Proximal end plate 480 has no central aperture (although it may have one during assembly to accommodate the distal end of the drive shaft 18), and it includes further teeth or distally-projecting bumps of a set 482, which are designated 482a, 482b, 482c, and 482d. Each tooth of sets 472 and 482 is in the form of a roughly triangular ramp, which may be somewhat rounded as shown, rather than straight-sided as in FIG. 3, depending upon the allowable or desired harmonic content.

Each of the end plates 470, 480 of FIGS. 4a and 4b may be affixed to the shell 422 by any conventional method. If they are made from metal, welding, brazing or soldering may be appropriate, whereas if they are made from composite materials or polymers, adhesives or chemical welding may be suitable. The shaft 18 may be affixed to proximal plate 480 in any manner. It is believed that forming a press-fit axial aperture in the proximal side (or all the way through) the proximal plate 480, and affixing the shaft in the axial aperture, with or without welding or adhesive, is most effective. In order to aid in assembly of the distal plate 470 and proximal plate 480 to the shell 422 with the teeth of the two plates in the appropriate rotational relationship, namely an alternating relationship, each of the end plates may include a key, as suggested by keys 473 and 483, which engage corresponding keys, as suggested by key 423 of FIG. 4a, in the ends of the shell. Preferably, these keys are selected to prevent incorrect assembly, as by providing three circumferentially-spaced keys 473 in conjunction with four keys 474; this prevents assembly of two end pieces of the same type to the shell. The relative positions of the teeth are set forth in the developed view of FIG. 3, and is suggested in FIG. 4b by dashed lines, such as dashed line 479c, which shows the location on proximal plate 480 above which tooth 472c is located. Similarly, dashed line 479a shows the location on proximal plate 480 above which tooth 472a is located, and dash line 479b shows the location on proximal plate 480 above which tooth 472b is located in the assembled motion converter. The illustrated locations for the teeth result in alternation of the circumferential positions of the upper (distal) and lower (proximal) teeth. This alternation of position, in turn, results in driving of a tab of a follower, during operation, in alternating directions by the alternating teeth.

Figure 4C:
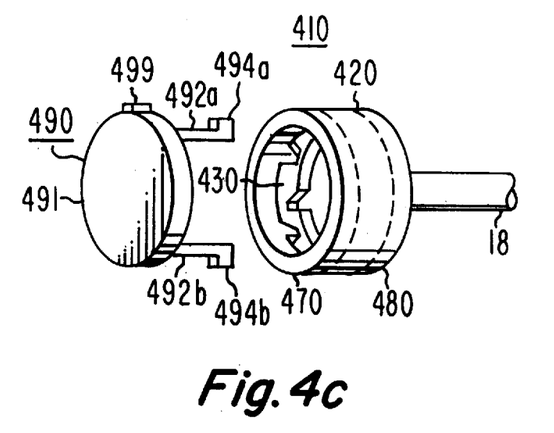

FIG. 4c illustrates a rotary-to-axial-motion converter 410 including the rotational driver made up of shell 422, assembled with distal end piece 470 and proximal end piece 480, and a portion of drive shaft 18, exploded away from the follower 490. As illustrated, follower 490 includes a body 491, legs 492a and 492b, and outwardly-extending tabs or protuberances 494a and 494b. The legs 492a and 492b are mounted on the body 491 at locations selected so that the legs extend through aperture 471 in distal end plate 470, and so that the protuberances 494a and 494b extend into the groove within cavity 428 of shell 422 formed by the spaced-apart end plates 470 and 480. While only two legs 492 and corresponding protuberances 494 are illustrated, there may be three or more legs and protuberances, depending upon the configuration of the groove 430. So far not discussed in conjunction with FIG. 4c is some means for preventing rotation of the follower 490 in consonance with the rotational driver 420. This function is performed in any desired manner, as for example by the use of a key 499 which engages a corresponding key slot in a housing, not illustrated in FIG. 4c.

Figure 5:
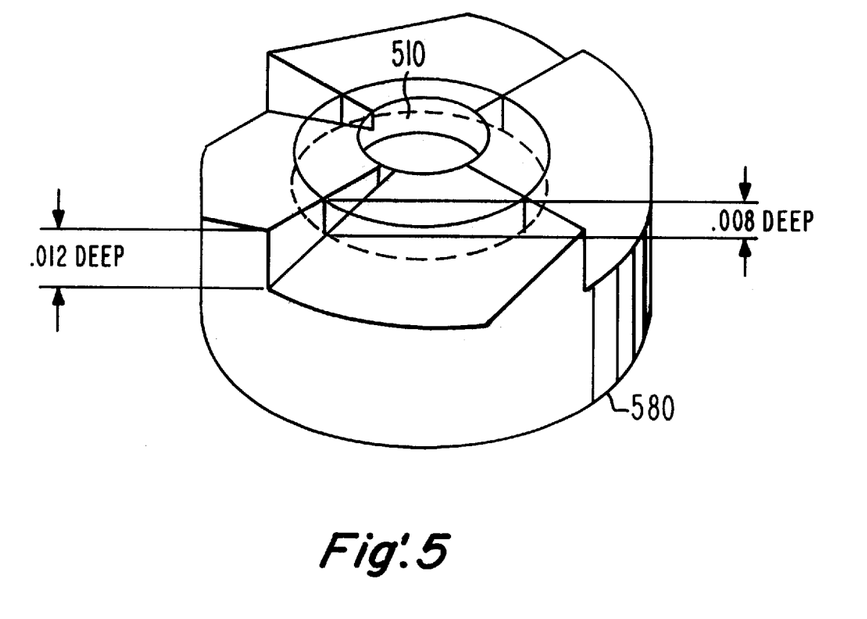
FIG. 5 is a perspective or isometric view of a somewhat different embodiment of an end piece, which includes an aperture for accommodating the distal end of the shaft.

FIG. 5 illustrates another possible configuration of teeth on an end piece. As illustrated in FIG. 5, the teeth are straight ramps separated by flat floors.

Figure 6:
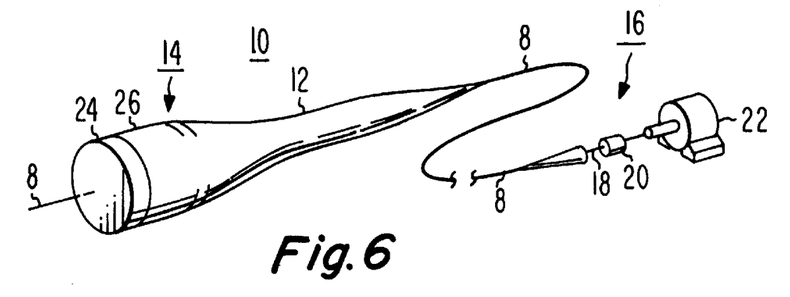
FIG. 6 is a simplified perspective or isometric view of a catheter according to the invention, with its drive motor.

FIG. 6 is an overall view of a catheter 10 according to an aspect of the invention, including a flexible body 12 defining a distal end 14 and a proximal end 16. A portion of body 12 is illustrated as a single line following a local axis 8. Local axis 8 is parallel to the flexible body 12 at any location along the flexible length of the body. As illustrated in FIG. 6, the distal end of catheter 10 includes an enlarged portion 26 which houses the rotary-to-axial-motion converter according to the invention, such as 210 of FIG. 2a or 410 of FIG. 4c. At the distal end of the catheter 10, the follower 24 of a rotary-to-axial-motion converter (not visible in FIG. 6) is exposed, for coupling motion to a surrounding biological fluid (also not illustrated) within the patient's body. At the proximal end of catheter 10, the shaft 18 protrudes, and is adapted to be driven by a rotational drive motor, illustrated as an electrical motor 22. A coupler illustrated as 20 may be attached to the shaft 18 to aid in coupling to the motor output shaft. The coupler 20 may be no more than a cylindrical shell having a through aperture dimensioned at each end to the diameter of the associated shaft, together with setscrews or other means for holding the coupler to each shaft. At the distal end of catheter 10, the braiding is made larger, to accommodate the bulk of the motion converter. This larger portion is illustrated as region 26 of FIG. 6.

Figure 7A:
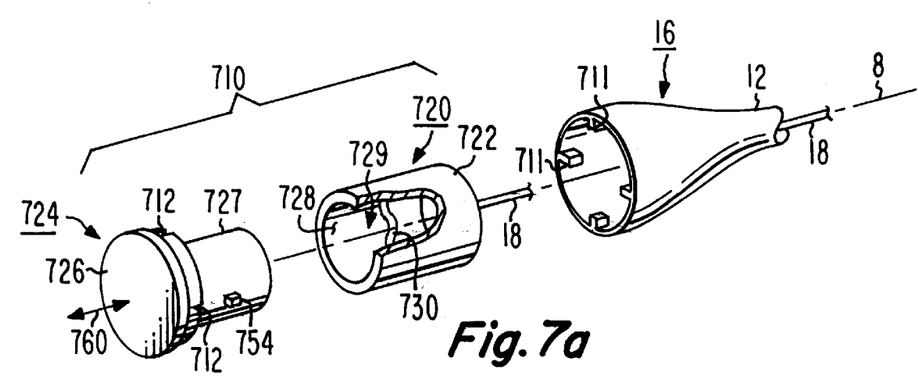
FIG. 7a is a simplified, exploded view of a distal portion of the catheter of FIG. 6.
Figure 7B:
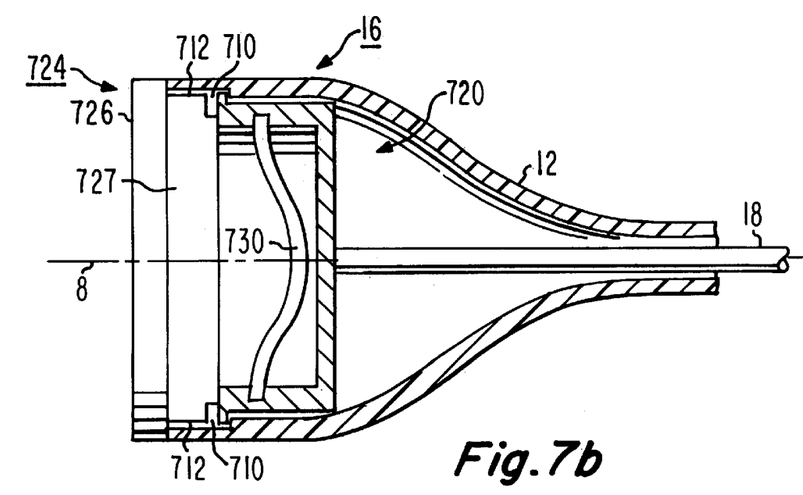
FIG. 7b is a cross-sectional view of the assembled distal end.

FIG. 7a illustrates the distal end 14 of the braided catheter body 12, exploded away from a motion converter according to an aspect of the invention. In FIG. 7a, the expanded portion 26 of body 12 can be seen to include keys illustrated as 711, which mate with corresponding keys 712 in a follower 724. Follower 724 of rotary-to-axial motion converter 710 has a bipartite or two-part body with a larger-diameter distal portion 726 and a smaller-diameter proximal portion 727. Portion 727 of follower 724 is small enough to fit within the cavity 729 of rotary drive shell 720, clear of cavity inner surface 728, with its protuberance 754 engaged with depressed groove 730. The arrangement of FIG. 7a thus includes a single "leg" 727, which supports one or more groove-engaging protuberances 754. The larger-diameter distal portion 724 of FIG. 7a is that portion of the follower which is illustrated as 24 in FIG. 6. Rotation of the shaft, with shell 720 and groove 730, causes the protuberance 754 to be translated axially in a reciprocal manner in the direction of arrow 760. The arrangement of FIGS. 7a and 7b has a single "leg" for the follower, which supports as many of the radially projecting, groove-engaging protuberances, such as 754, as may be desired. However, this form of follower has the disadvantage that its mass will tend to be greater than that of a corresponding follower which has one or more discrete legs which support the protuberances, and as a result may tend to have a lower maximum operating frequency as a result of maximum torque limitations.

According to an aspect of the invention, the body 12 of the catheter 10 of FIG. 6 is made from a braided tube of flexible material such as polymer thread. The braided material can be made to any diameter along its length. The braiding of thread, including polymer thread, into such structures is well known. The braided body may be impregnated with a flexible sealant, such as polyethylene, to prevent leakage of body fluids into the interior of the catheter, and to maintain the shape of the catheter body. The method for making the catheter body according to this technique is to braid a tube or sleeve, expand the braided tube/sleeve at the distal end, and fit it over a mandrel having the appropriate shape of the catheter body, and also having grooves which will form the basis for key projections 711. Once fitted over the mandrel, the braided tube/sleeve is impregnated with a curable polymer, and then vacuum-bagged to press the impregnated tube/sleeve closely against the mandrel. The vacuum-bagged impregnated tube/sleeve fitted over the mandrel is then subjected to heat to cure the polymer impregnant. As an alternative to heat, the impregnant may be a time-cured material, such that curing does not take place until an appropriate time period after mixing, to give time to perform the impregnating and vacuum bagging steps of the method.

In order to provide a flywheel effect which limits the transfer of drive torque variations to the shaft, the mass of the rotary driver should exceed the mass of the follower. This may be accomplished by use in the rotary driver of a greater amount of material than in the follower, or the use of material of greater density in the rotary driver than in the follower, or both.

Thus, an acoustic ablation catheter (10) according to the invention comprises an elongated catheter body (12) defining distal (14) and proximal (16) ends. An elongated drive shaft (18) extends from near the proximal end (16) to near the distal end (14) of the catheter body (12). A coupling arrangement (20) may be coupled to the shaft (18) at a location near the proximal end (16) of the body, adapted for coupling the shaft (18) to a rotary driver (22), such as an electric motor, whereby, when so coupled, the shaft (18) is driven in a rotary manner. A rotary-to-axial motion converter (210, 410) is coupled to the shaft (18) near the distal end (14) of the catheter body (12), for, when driven in a rotary manner by the shaft (18), converting the rotary motion into axial motion, and for coupling the axial motion to a surrounding biological medium.

The rotary-to-axial motion converter (210, 410) of the catheter (10) further comprises a rotary driver (220, 420, 720) coupled to the shaft (18), for being driven in a rotary manner thereby in response to rotation of the shaft (18). The rotary driver (220, 420, 720) includes a cylindrical shell (222, 422, 722) with an outer surface (223) having the general shape of a right circular cylinder defining distal (224) and proximal (226) ends. The cylindrical shell (222, 422, 722) also defines an inner surface (228, 428, 728) with a guide path (230, 330, 430, 730) which is circumferentially continuous about the inner surface (228, 428, 728) of the shell (222, 422, 722). The guide path (230, 330, 430) has portions (230d) which lie closer to the distal end (214) of the cylindrical shell (222) and other portions (230p) which lie closer to the proximal end (216) of the shell (222).

The rotary-to-axial motion converter (210, 410, 710) of the catheter (10) also comprises a follower (250, 490, 724) coupled to the guide path (230, 330, 430, 730). The body (251, 491, 726) of the follower (250, 490, 724) is fixed against rotation (by, for example, tabs 256 or 711), so it cannot rotate with the rotary driver (220, 420, 720). The follower (250, 490, 724) is mechanically coupled to the guide path (230, 330, 430, 730), for being reciprocally driven in an axial manner in response to rotation of the shaft (18), shell (220, 420, 720), and guide path,(230, 330, 430, 730).

In a particular embodiment of the invention, the catheter body (12) is flexible, so that its shaft (18) defines a local axis (8) at various locations along the catheter. The cylindrical shell (220, 420, 720) is centered about at least an extension of the local axis (8). The guide path (230, 330, 430, 730) is formed by, or includes or comprises, a depressed groove (230, 330, 430, 730) formed in the inner surface (228, 428, 728) of the cylindrical shell (220, 420, 720); this depressed groove (230, 330, 430, 730) is depressed relative to the cylinder inner surface "land" area (228, 428, 728). The follower (250, 490, 724) includes at least one tab or projection (254a, 254b; 494a, 494b; 754) extending radially away from the local axis (8) for being mechanically coupled into the depressed groove (230, 330, 430, 730) of the cylindrical shell (220, 420, 720). When the shaft (18) rotates, the cylindrical shell (220, 420, 720) also rotates, carrying the depressed-groove guide path (230, 330, 430, 730) with it. The follower projection (254a, 254b; 494a, 494b; 754) rides in the groove (230, 330, 430, 730), and is therefore translated axially with a continuous reciprocal motion (arrow 260, 760).

In a particularly advantageous embodiment of the invention, the rotary driver (420) and the depressed-groove guide path (330, 430) is made up of at least a cylindrical shell (422) having an inner cavity (429) with a smooth inner surface (428), meaning an inner surface without a distinct guide path, together with one or more end pieces or inserts (470, 480), which may be annular (470) or solid (480). The end pieces (470, 480) are dimensioned to fit at or near the end of the cylinder (420) or within the cavity (429) of rotary driver (420) shell (422). The end pieces (470, 480) have outward axial projections or teeth (472, 482) which define portions of the depressed groove guide path (330, 430). The follower (490) includes at least one tab or radial projection (494a, 494b) which fits into the guide path (330, 430). When the shaft (18) rotates, the rotational drive cylinder (420) shell (422) with its inner groove (330, 430) rotates. At any fixed point around the periphery of the groove (330, 430), the groove effectively moves with a reciprocal axial motion in response to rotation of the cylinder (420) with its end pieces (470, 480). The tab or projection (494a, 494b) of the follower (490) is mechanically coupled to the groove (330, 430), and the follower (490) itself is prevented from rotating (tab 499), and as a consequence the tab or projection (494a, 494b), and the follower (490) itself, moves axially with a reciprocal motion.

A method for fabrication of the body of the catheter according to an aspect of the invention involves braiding threads to form a tube. A braided tube has the property that its diameter can be expanded or contracted at particular locations along its length, as in the well-known child's "finger trap," once known as a "Chinese finger trap." The distal end of the braided tube is expanded to fit over a mandrel having the shape of the body of the catheter, including the enlarged distal portion. The mandrel may also have cutouts located so as to define, after impregnation, monolithically integral keys such as 711. The braided tube is impregnated with uncured liquid polymer, such as epoxy. The combination of the impregnated tube and the mandrel is vacuum bagged, and then the impregnant is cured, either by heat or by time, or both. All of these steps are individually known in the arts of fabrication of composite materials, and the method according to the invention will be apparent to those skilled in the art from the above description, taken in conjunction with the illustrations of the body to be fabricated.

Other embodiments of the invention will be apparent to those skilled in the art. For example, the illustrated catheter may have additional lumens for infusion of medication or for aspiration of substances from the body. The catheter may have additional lumens for carrying electrical wires for electrical equipment at the distal end of the catheter, it may include a fiber optic scope or a camera arrangement, it may include a balloon, and in general may include any of those devices or apparatuses which are conventional in a catheter arrangement. The teeth of the end plates of the rotary driver of the motion converter may be of any shape; those skilled in the art will recognize that the relative harmonic content of the acoustic waves resulting from use of the catheter will depend upon the shape and spacing of the bumps or teeth 472, 482. Also, increasing the number of teeth which are contacted by the follower during each revolution of the rotary driver tends to increase the fundamental frequency, and reducing the number of teeth tends to reduce the fundamental frequency. While the embodiment of FIGS. 6, 7*a* and 7*b* has been shown as having the distal portion 726 of the follower 724 larger than the diameter of the shell 720, and substantially equal to the diameter of the body 12, the diameter of distal portion 724 could be equal to the inner diameter of the distal end of the body 12, so that the distal end of the follower could lie within the envelope defined by body 12. While four projections or ramps 472, 482 have been illustrated on each side of the groove 430 in FIGS. 4*a*, 4*b*, and 4*c*, any number of such ramps may be used, with a change in the fundamental frequency of the resulting sound energy attendant thereupon. Naturally, the groove defined between the teeth of the bearing surfaces may have any desired profile, selected to provide the desired acoustic signature. The tabs which mate with the groove may be square as illustrated, or round, or may in general have any shape which is suited to engaging the groove.

What is claimed is:

1. An acoustic ablation catheter, comprising:

an elongated catheter body defining distal and proximal ends;

an elongated drive shaft extending from near said proximal end to near said distal end of said body;

coupling means coupled to said shaft near said proximal end of said body, adapted for coupling said shaft to rotary drive means, whereby, when so coupled, said shaft is driven in a rotary manner;

rotary-to-axial motion conversion means coupled to said shaft near said distal end of said catheter body, for, when driven in a rotary manner by said shaft, converting said rotary motion into axial motion, said rotary-to-axial motion conversion means further comprising (a) rotary drive means coupled to said shaft for being driven in a rotary manner thereby in response to rotation of said shaft, said rotary drive means including a cylindrical shell with an outer surface having the general outer shape of a right circular cylinder defining distal and proximal ends, said cylindrical shell also defining an inner surface defining a guide path which is circumferentially continuous about the circumference of said inner surface of said shell, and which guide path has portions which lie closer to said distal end of said cylindrical shell and other portions which lie closer to said proximal end of said shell, (b) a follower coupled to said guide path, said follower being fixed against rotation with said rotary drive means, said follower also being mechanically coupled to said guide path, for being reciprocally driven in an axial manner in response to rotation of said shaft, shell, and guide path.

2. A catheter according to claim 1, wherein:

said shaft defines a local axis at any location along said shaft;

said cylindrical shell is centered about at least an extension of said local axis;

said guide path comprises a depressed groove formed in said inner surface of said cylindrical shell; and said follower comprises at least one tab extending radially away from said local axis for being mechanically coupled to said depressed groove of said cylindrical shell.

3. A catheter according to claim 1, wherein said guide path, when developed about an axis of said catheter, traces a sinusoidal path.

4. A catheter according to claim 1, wherein said guide path, when developed about an axis of said catheter, traces a path including ramp-like projections which alternate between distally-directed ramps and proximally-directed ramps.

5. A catheter according to claim 4, wherein each of said ramps includes at least two straight-sided portions.

6. A catheter according to claim 5, wherein said straight-sided portions of said ramps have different lengths.

7. A catheter according to claim 5, wherein said straight-sided portions may be separated by a curved portion.

8. A catheter according to claim 1, wherein the mass of said rotary drive means exceeds the mass of said follower.

* * * * *